(12) United States Patent
Singh et al.

(10) Patent No.: US 9,194,842 B2
(45) Date of Patent: Nov. 24, 2015

(54) THERMAL ACOUSTIC IMAGING METHODS, SYSTEMS, AND APPARATUS FOR DETECTING DEFECTS IN AN OBJECT

(75) Inventors: Surendra Singh, Chandler, AZ (US); Robert Hogan, Chandler, AZ (US); Frederick William Vensel, Gold Canyon, AZ (US)

(73) Assignee: HONEYWELL INTERNATIONAL INC., Morris Plains, NJ (US)

( * ) Notice: Subject to any disclaimer, the term of this patent is extended or adjusted under 35 U.S.C. 154(b) by 937 days.

(21) Appl. No.: 13/165,394

(22) Filed: Jun. 21, 2011

(65) Prior Publication Data
US 2012/0330569 A1 Dec. 27, 2012

(51) Int. Cl.
| | | |
|---|---|---|
| *G01N 29/04* | (2006.01) | |
| *G01N 29/06* | (2006.01) | |
| *G01N 29/34* | (2006.01) | |
| *G01N 29/46* | (2006.01) | |

(52) U.S. Cl.
CPC ............ *G01N 29/043* (2013.01); *G01N 29/069* (2013.01); *G01N 29/0654* (2013.01); *G01N 29/348* (2013.01); *G01N 29/46* (2013.01); *G01N 2291/044* (2013.01)

(58) Field of Classification Search
CPC .............. G01N 29/043; G01N 29/069; G01N 29/0654; G01N 29/348; G01N 29/46; G01N 2291/044
USPC .......................................... 702/39, 40, 35, 36
See application file for complete search history.

(56) References Cited

U.S. PATENT DOCUMENTS

| | | |
|---|---|---|
| 4,389,891 A | 6/1983 | Fournier |
| 6,186,004 B1 | 2/2001 | Kaduchak et al. |
| 6,698,288 B2 | 3/2004 | Shirzad et al. |
| 6,838,670 B2 | 1/2005 | Lewis et al. |
| 6,886,407 B1 * | 5/2005 | Fredenberg ..................... 73/622 |
| 7,057,176 B2 | 6/2006 | Rothenfusser et al. |
| 7,060,971 B2 | 6/2006 | Zombo et al. |
| 7,119,338 B2 | 10/2006 | Thompson et al. |
| 7,131,331 B2 | 11/2006 | Bates |
| 7,199,367 B2 | 4/2007 | Favro et al. |

(Continued)

OTHER PUBLICATIONS

Moles, Michael et al. "Ultrasonic Phased Arrays," Advanced Materials and Processes (Mar. 2007). pp. 37-40.*

*Primary Examiner* — Sujoy Kundu
*Assistant Examiner* — Liam R Casey
(74) *Attorney, Agent, or Firm* — Ingrassia Fisher & Lorenz, P.C.

(57) ABSTRACT

Thermal Acoustic Imaging (TAI) methods and systems are provided for detecting defects in an object. The TAI system may include a plurality of acoustic wave transceivers (AWTs), which are positioned around the object at different locations, and a broadband frequency signal generator, which is coupled to each of the AWTs. The system may further include an acoustic processor configured to utilize the AWTs to gather acoustic data pertaining to the object, process the acoustic data to generate spectral response data, and then process the spectral response data to determine an optimized setup. The optimized setup may include optimized excitation frequencies and optimized inspection positions for positioning a plurality of infrared imaging devices at different locations around the object. A plurality of infrared imaging devices may then be selectively positioned with respect to the object at the optimized inspection positions and utilized to further inspect the object for defects.

17 Claims, 12 Drawing Sheets

(56) References Cited

U.S. PATENT DOCUMENTS

| | | |
|---|---|---|
| 7,297,952 B2 | 11/2007 | Raulerson et al. |
| 7,513,964 B2 | 4/2009 | Ritter et al. |
| 7,549,339 B2 | 6/2009 | Staroselsky et al. |
| 7,709,794 B2 | 5/2010 | Zhao et al. |
| 7,711,452 B2 | 5/2010 | Konstadinidis et al. |
| 7,855,368 B2 | 12/2010 | Zalameda et al. |
| 2003/0010124 A1 | 1/2003 | Bates |
| 2005/0241397 A1* | 11/2005 | Bergman ............... 73/606 |
| 2007/0016044 A1* | 1/2007 | Blalock et al. ............ 600/443 |
| 2007/0045544 A1* | 3/2007 | Favro et al. ............ 250/341.6 |

* cited by examiner

THERMAL ACOUSTIC IMAGING METHODS, SYSTEMS, AND APPARATUS FOR DETECTING DEFECTS IN AN OBJECT

TECHNICAL FIELD

The disclosed embodiments generally relate to systems, methods and apparatus for detecting defects in an object, and more particularly to Thermal Acoustic Imaging (TAI) methods, systems and apparatus for detecting defects in an object being inspected.

BACKGROUND

It is often important to establish and/or verify structural integrity of objects, components and structures. Loss of structural integrity in an object can be caused by material defects.

Non-Destructive Evaluation (NDE) methods refer to a class of methods that can be used to inspect objects for defects. NDE methods are often used to inspect materials for defects, such as structural anomalies, inclusions, cracks, etc. However, many conventional NDE methods often provide incomplete or otherwise inadequate inspections.

Recently, non-destructive evaluation methods commonly referred to as Thermal Acoustic Imaging (TAI) (or alternatively as acoustic thermography, sonic IR, thermosonic imaging, etc.) have been developed for detecting defects in objects in a fast and cost-effective manner. In general, TAI techniques use ultrasonic energy to excite an object being inspected, which causes the object and defective features therein to generate heat, which can then be detected using infrared (IR) imaging technologies.

In one exemplary TAI technique, an object that is being inspected is coupled to an ultrasonic broadband transducer. The ultrasonic broadband transducer is excited so that it couples a broadband acoustic signal into the object, which that introduces broadband sound energy into the object via acoustic waves. As acoustic waves are introduced into the object, the acoustic waves will cause defects in the object to vibrate.

To explain further, defects normally include opposing surfaces or interfaces, such as opposing edges of a crack, that move with respect to and against one another as the object is subjected to acoustic waves. Because the surfaces do not ordinarily vibrate in unison, they will rub against each other, which results in friction between or in the vicinity of the surfaces. Friction between the surfaces generates heat. Defects present in the object will heat up at a greater rate than other defect-free portions of the object, which are only minimally and uniformly heated. As temperature increases in the vicinity of the defect, infrared cameras or sensors can be used to detect defects that are discernable from other defect-free areas.

An infrared (IR) imaging device, such as thermal or infrared imaging camera, can then be used to capture images of the object that can be used to detect variations in temperature or infrared energy. For example, in some implementations, infrared energy can be detected using an IR camera that includes a two dimensional array of infrared detectors (pixels). Each pixel generates a signal that can be processed by an image processor to generate images. High resolution images can be captured by subtracting a background image (taken before acoustic excitation) from image(s) taken after excitation and recording the time derivative of the signal from each pixel instead the signal itself. Defects in the object will appear in the images as brighter areas in contrast to darker background areas that represent defect-free areas of the object.

Thus, thermal acoustic imaging techniques that combine acoustic induced heating with infrared imaging can be used as part of a very efficient, non-destructive defect detection system that can allow defects to be detected without needing to damage the object.

Although TAI techniques have proven successful for detecting defects in some objects in some environments, some presently available TAI techniques have drawbacks and limitations. For example, some presently available TAI systems can analyze only small areas (e.g., small objects or areas of objects), and are generally restricted to laboratory use. This can make it a difficult and time-consuming endeavor to inspect large objects or objects having a complex shape or geometry. Existing TAI techniques can often be complex to use when the object is particularly large and/or complex in shape and has many different areas or regions that require independent inspection.

In order for the TAI technique to work correctly, the IR imaging device must be positioned correctly and aimed at the correct location where defects might be located. If not, there is a risk that the imaging device will not detect the heat that is generated, and the defect may not be detected. This can happen for example, when the IR imaging device does not cover the entire surface of the object or is not aimed at the correct location of the defect. In addition, when a tight crack and a node are co-located (i.e., located in the same location), the IR imaging device may not be able to detect the presence of the crack since the object will not vibrate in that location.

It would be desirable to provide improved TAI methods, systems and apparatus for detecting defects, such as tight cracks, in an object being inspected. Furthermore, other desirable features and characteristics of the present invention will become apparent from the subsequent detailed description of the invention and the appended claims, taken in conjunction with the accompanying drawings and this background of the invention.

BRIEF SUMMARY

One challenge in successfully implementing such TAI methods relates to deciding where the IR imaging device should be positioned and pointed towards with respect to the object that is being evaluated or inspected for defects. This involves determining and locating regions of interest (ROIs) of the object that are particularly susceptible to developing defects, and then correctly aiming the IR imaging device at the ROIs so that the defects can be successfully detected. This is especially true as the defects that are sought to be detected become smaller and/or when the object being inspected is large in size and/or has a complex shape.

Transfer of mechanical energy (e.g., acoustic waves) through the object has a frequency dependence that depends on, for example, the size, shape and materials characteristics of the object. Excitation of defects is dependent upon the location of the defect, the geometry of the object and the intensity and spectrum of the acoustic energy introduced into the object. Thus, another challenge in successfully implementing such TAI methods relates to selection of the proper frequency ranges that should be used to generate the acoustic waves used to excite the object so that appropriate vibration modes of the object are excited. As such, it is important to understand the relationship between the vibration modes of an object with respect to region of interests (ROIs) for that object.

In accordance with the disclosed embodiments, Thermal Acoustic Imaging (TAI) methods, systems and apparatus are provided for detecting defects in an object being inspected.

The disclosed embodiments can allow an optimized setup to be defined for detecting defects in the object. This optimized setup can include optimized locations or positions of IR cameras with respect to the object, as well as optimized excitation frequencies that should be used to excite defects in the object to cause defects to vibrate with maximum or near maximum amplitude.

In accordance with one embodiment, a method is provided for detecting defects in an object. In accordance with the disclosed embodiments, a plurality of acoustic wave transceivers (AWTs) are positioned around the object at different positions so that all regions of interest of the object are within an acoustic field of view of at least one of the AWTs.

A broadband acoustic energy signal is generated that comprises a plurality of excitation frequencies of potential interest. The excitation frequencies of potential interest can be determined based on physical characteristics of object and corresponding vibration modes of object. Acoustic waves can then be generated based on the broadband acoustic energy signal, and transmitted from each of the AWTs toward the object. In some implementations, the acoustic waves can be separately and sequentially transmitted from each of the AWTs toward the object to separately transmit to or "interrogate" different regions of the object. The transmitted acoustic waves couple broadband acoustic energy to the object over excitation frequencies of potential interest. The broadband acoustic energy causes excitation of the defects to induce motion of the defects and cause the defects to vibrate at different frequencies that depend on the material properties, dimensions and/or geometry of the object. The defects generate acoustic waves in response to the transmitted acoustic waves, and these acoustic waves can be received at one or more of the AWTs.

Received acoustic waves from the object can then be detected at each of the AWTs. For example, each of the AWTs can detect the acoustic energy (via the received acoustic waves) that corresponds to vibrations induced in the object to produce a signal that can be processed to acquire an acoustic spectral response of the object to the transmitted acoustic waves over the excitation frequencies of potential interest. The received acoustic waves from the object can be processed to generate spectral response data that corresponds to each of the AWTs, and the spectral response data can then be processed to determine an optimized setup comprising optimized excitation frequencies and optimized position information.

The optimized position information for particular ones of AWTs corresponds to particular regions of interest of the object that have been determined to correspond to potential locations of defects in the object. Based on the optimized position information for the AWTs, optimized inspection positions for infrared imaging devices can be determined A plurality of infrared imaging devices can then be selectively positioned with respect to the object at the optimized inspection positions. This way each infrared imaging device are selectively aimed at the particular regions of interest of the object that have been determined to correspond to potential locations of defects in the object.

Other acoustic waves can then be transmitted to the object that are generated based on a second broadband acoustic energy signal. The second broadband acoustic energy signal comprises the optimized excitation frequencies that will result in optimized interactions (e.g., improved vibration amplitudes) between and object and an acoustic energy source when the acoustic energy source is excited at the optimized excitation frequencies.

Heat generated by the defects results has a detectable thermal response. Each of the infrared imaging devices can generate a time series of infrared images of a particular one of the regions of interest of the object (e.g., of a portion of the object that they are aimed at), based on IR signals received from the object as the defects vibrate over a time interval, and can record the time series of infrared images. The time series of infrared images can be processed in contrast to a reference image to generate a composite infrared image that includes a thermal signature that represents a discernable emission of infrared energy by the object, or a portion of the object, that is indicative of an amount of infrared energy generated or emitted by a particular defect in the object (and that is distinguishable or discernable from background heat or infrared energy generated by non-defective portions of the object).

BRIEF DESCRIPTION OF THE DRAWINGS

The present invention will hereinafter be described in conjunction with the following drawing figures, wherein like numerals denote like elements.

DETAILED DESCRIPTION

Figure 1A:
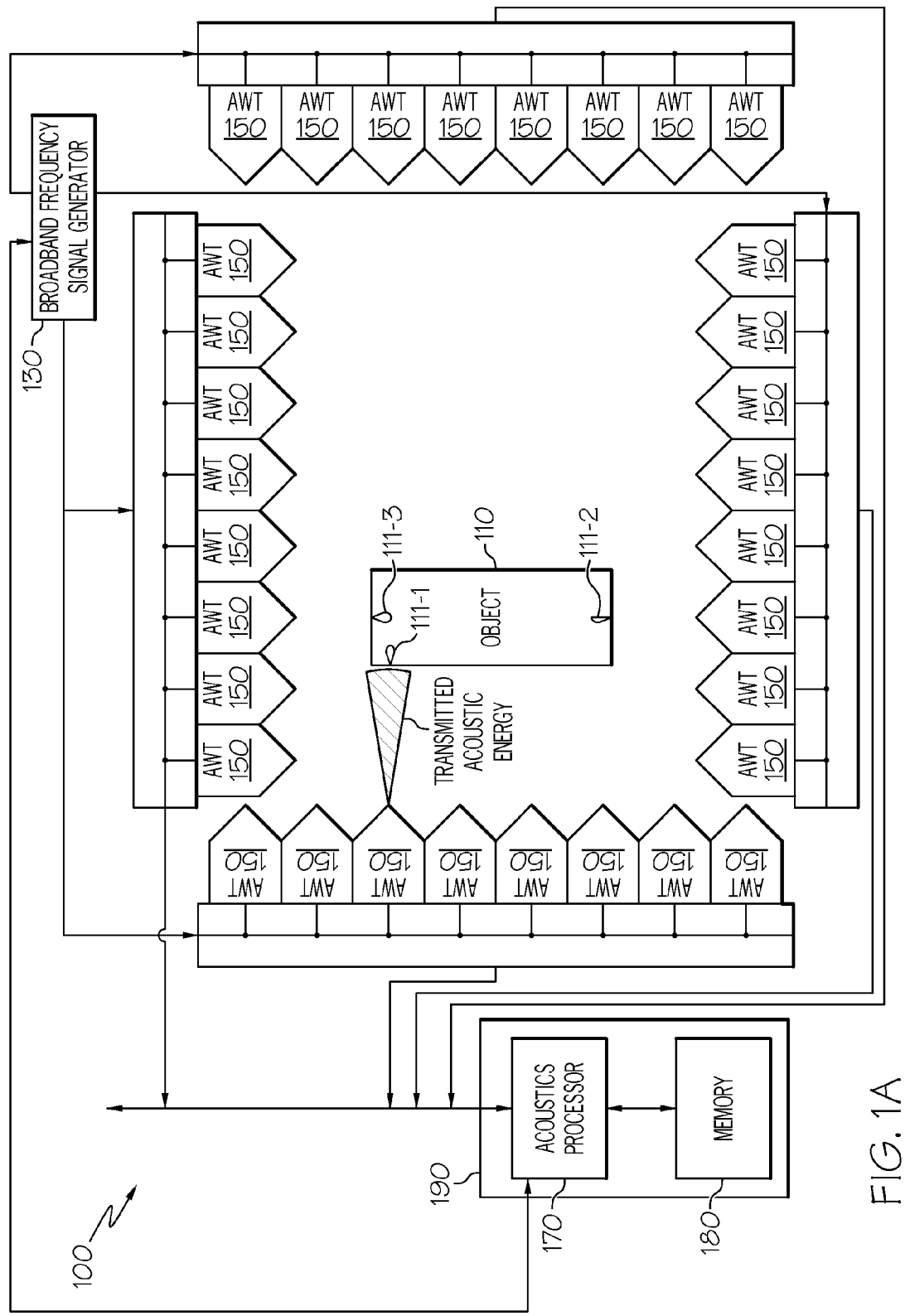
FIGS. 1A through 1F are block diagrams of a system in accordance with an exemplary embodiment.

The following detailed description is merely exemplary in nature and is not intended to limit the invention or the application and uses of the invention. As used herein, the word "exemplary" means "serving as an example, instance, or illustration." Any embodiment described herein as "exemplary" is not necessarily to be construed as preferred or advantageous over other embodiments. Furthermore, there is no intention to be bound by any theory presented in the preceding background or the following detailed description.

FIGS. 1A through 1F are block diagrams of a system 100 in accordance with an exemplary embodiment.

The system 100 includes an object 110 that is being inspected or evaluated, a broadband frequency signal generator 130, and a plurality of acoustic wave transceivers (AWTs) 150 that can be used to collectively implement a phased acoustic array. As used herein, the term "acoustic wave transceiver" refers to an apparatus that is designed to transmit acoustic waves and to receive acoustic waves. Preliminarily, it is noted that in FIGS. 1A-1F, transmitted acoustic energy and received acoustic energy is represented as having a particular profile; however, this is not intended to illustrate an actual representation of the profiles of the transmitted acoustic energy and received acoustic energy. Rather, it is merely intended to represent acoustic energy being transmitted from one of the AWTs 150 towards the object 110 or to represent acoustic energy being received by one or more of the AWTs 150 from the object 110.

An acoustic wave transceiver can include an acoustic wave source or driver that transmits acoustic waves towards the object 110, and an acoustic wave sensor that receives/detects "received" acoustic waves that are received from the object 110 (or are that are generated by the object 110) in response to the transmitted acoustic waves. Depending on the implementation, the transmitting and receiving portions of the acoustic wave transceiver can be implemented in a single module (e.g., two modules within one housing) or using separate or different modules, but will be referred to herein as a single unit for sake of brevity. In addition, in some implementations, the transmitting and receiving portions of the acoustic wave transceiver can be implemented using the same physical apparatus and operating it in different transmitting and receiving modes.

The object 110 that is being inspected or evaluated can be any structure. As used herein, the term "object" refers to any structure, or a portion thereof, and may comprise any known material that is capable of including one or more defects. As used herein, a defect can be a surface defect or subsurface defect in an object. Defects can refer to disbonds, delaminations, tight cracks, corrosion, embedded contaminants, inclusions, voids, other internal interfaces and other types of defects that can exist within an object.

A broadband frequency signal generator 130 is coupled to each of the AWTs 150, and is designed to generate a broadband acoustic energy signal that is provided to each of the AWTs 150. The broadband acoustic energy signal comprises a plurality of excitation frequencies of potential interest that are spread out over a broad bandwidth of spectrum that spans between about 1 Hz and about 15 MHz. The plurality of excitation frequencies of potential interest can be determined based on physical characteristics (e.g., material properties, shape, weight, dimensions, and/or geometries) of object 110 and corresponding vibration modes of object 110.

The AWTs 150 can be positioned around the object 110 and used to transmit acoustic waves toward the object 110. FIGS. 1A through 1F illustrate AWTs 150 positioned at different locations with respect to the object 110; however, these locations are exemplary only and not intended to be limiting. In addition, due to two-dimensional limitations of the block diagrams, the AWTs 150 are illustrated at different locations in a two-dimensional space; however, those skilled in the art will appreciate that the AWTs 150 can be positioned at any location with respect to the object 110 in a three-dimensional space. Any number of AWTs 150 can be deployed at different positions with respect to the object 110 so that all regions of interest of the object are within an acoustic field of view of at least one of the AWTs 150. In FIGS. 1A-1F, the AWTs 150 are represented via a particular shape; however, their representation in these block diagrams is not intended to convey any type of structural limitation regarding the actual physical shape of the AWTs 150 or to imply that the AWTs 150 have a particular shape that is used in these block diagrams. The AWTs 150 can have any shape that is known in the art for acoustic wave transmitters and/or acoustic wave receivers.

In FIGS. 1A-1F, although thirty-two AWTs 150 are shown for purposes of illustration, there is no limitation on the number of AWTs 150 except that the number should be two or more. In other words, depending on the implementation any number of AWTs 150 can be deployed so long as at least two AWTs 150 are deployed at different positions/locations with respect to the object. The number of AWTs 150 deployed can vary depending on the implementation and be selected based on characteristics of the object 110 such as its geometry, shape, size, material characteristics, and the number and/or locations of regions of interest for that object. In addition, the AWTs 150 can be deployed at any position with respect to the object 110 so long as the AWTs 110 can receive acoustic waves generated by the object. In addition, although the AWTs 150 are illustrated as being separated from the object 110 in FIGS. 1A-1F and in acoustic communication with the object 110 over the air, in other implementations, the AWTs 150 can be placed in physical contact with the object 110 or indirect contact with the object 110 via an intermediate physical link. The only restriction is that the AWTs 150 should be able to acoustically communicate with the object 110.

In one embodiment, the acoustics processor 170 is designed to activate each of the AWTs 150 so that each AWT 150 generates and transmits acoustic waves (that are generated based on the broadband acoustic energy signal) toward the object 110.

In one implementation, the acoustics processor 170 is designed to separately and sequentially activate particular groups of the AWTs 150 (one at a time) so that each particular groups of AWTs 150 generates and transmits acoustic waves toward the object 110. Each particular group of the AWTs 150 can separately and sequentially transmit acoustic waves towards the object 110, for example, in a programmed pattern with relative time—or phase—shifts between their respective transmissions.

In another implementation, that is illustrated with reference to FIGS. 1A, 1C, and 1E, the acoustics processor 170 is designed to separately and sequentially activate each of the AWTs 150 (one at a time) so that each AWT 150 generates and transmits acoustic waves (that are generated based on the broadband acoustic energy signal) toward the object 110. Each of the AWTs 150 can separately and sequentially transmit acoustic waves to the object 110, for example, in a programmed pattern with relative time—or phase—shifts between their respective transmissions.

In accordance with some of the disclosed embodiments, each of the AWTs 150 can be sequentially excited (one at a time) over a broadband of frequencies by the broadband acoustic energy signal generated by the broadband frequency signal generator 130 such that each generates a broadband acoustic energy signal the comprises acoustic waves emitted over a broad spectrum that are transmitted towards the object 110 for a short period of time (e.g., between 0.1 milliseconds and 10 seconds).

As illustrated with reference to FIGS. 1A, 1C and IE, when each AWT 150 transmits or emits broadband ultrasonic or acoustic energy via acoustic waves towards the object 110 such that broadband acoustic energy is coupled to the object 110 which causes excitation of defects that resonate at many frequencies. Use of the broadband acoustic energy signal results in an appreciable increase in the induced motion within defects and causes vibration of defects of many sizes of interest to help ensure a thorough evaluation for defects. As such, the broadband acoustic energy signal provides improved defect detection capability for objects having complex geometrical component structures. The transmitted acoustic waves from a particular AWT excite the object over excitation frequencies of potential interest as frequency is varied. The broadband acoustic energy causes excitation of the defects 111 such that the defects 111 resonate at different frequencies. As illustrated with reference to FIGS. 1B, 1D and 1F, excitation induces motion of the defects 111 (e.g., causes the defects 111 to vibrate) and generate acoustic waves that correspond to vibrations induced in the object 110, which are referred to herein as "received" acoustic waves.

Figure 1B:
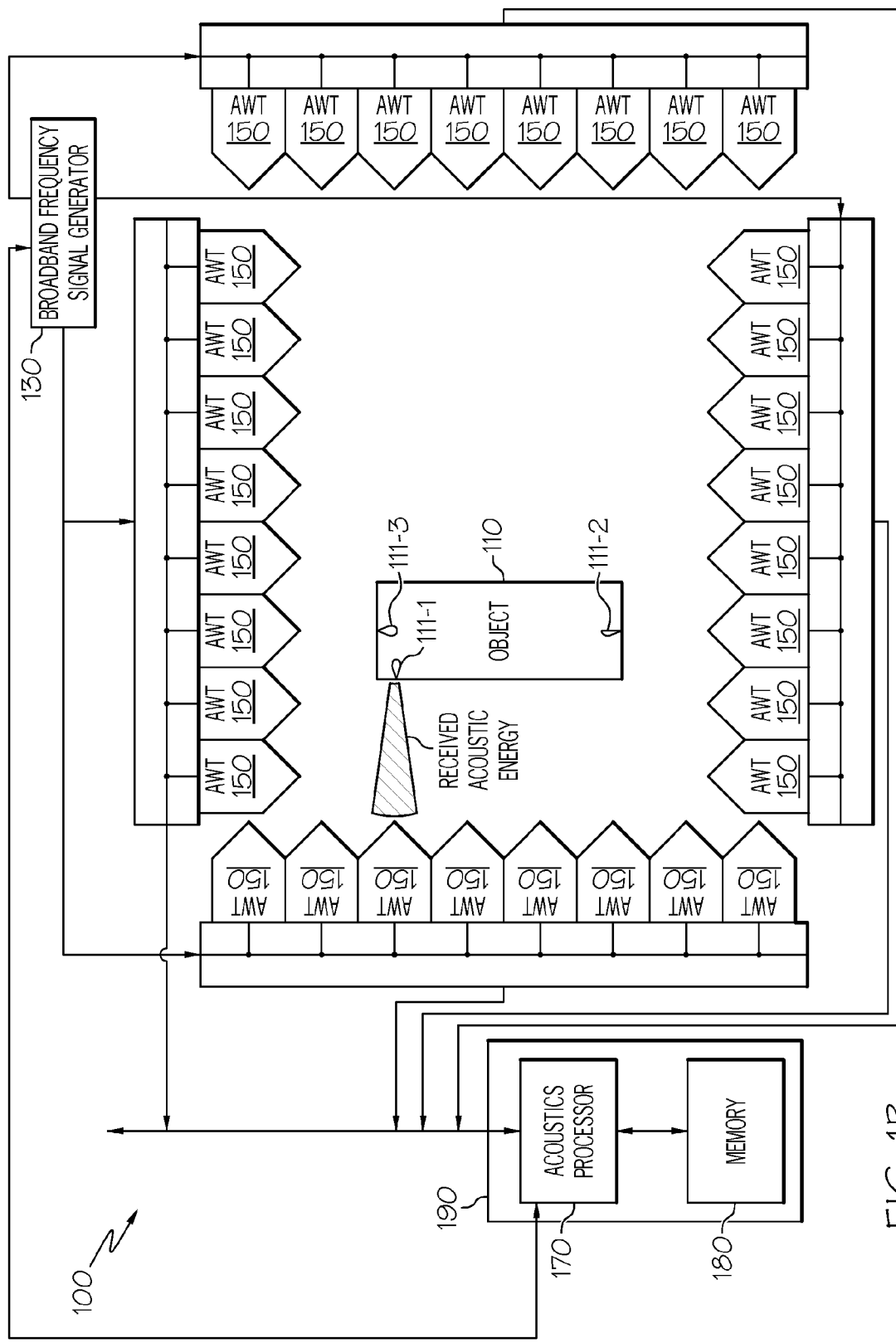
Figure 1C:
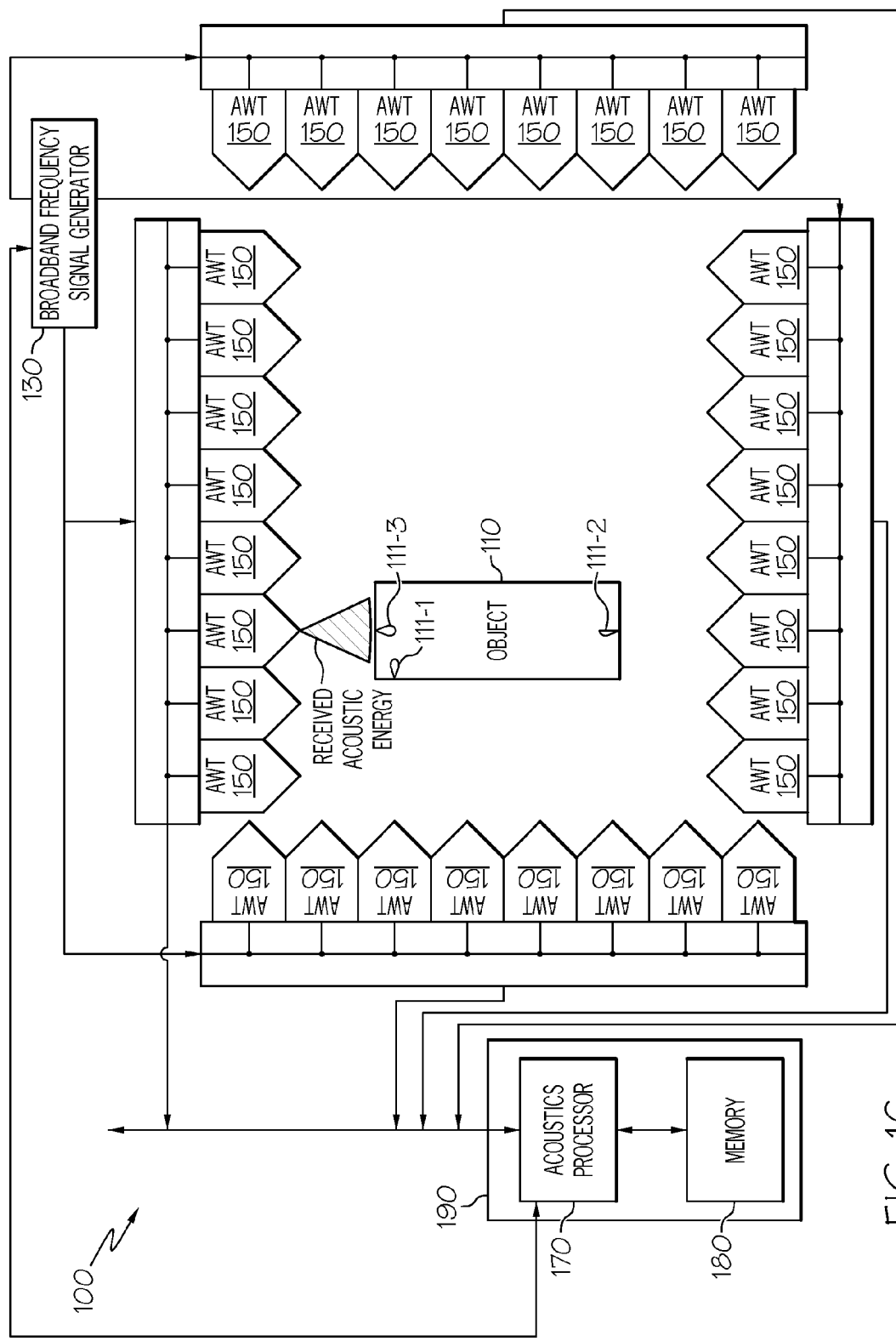
Figure 1D:
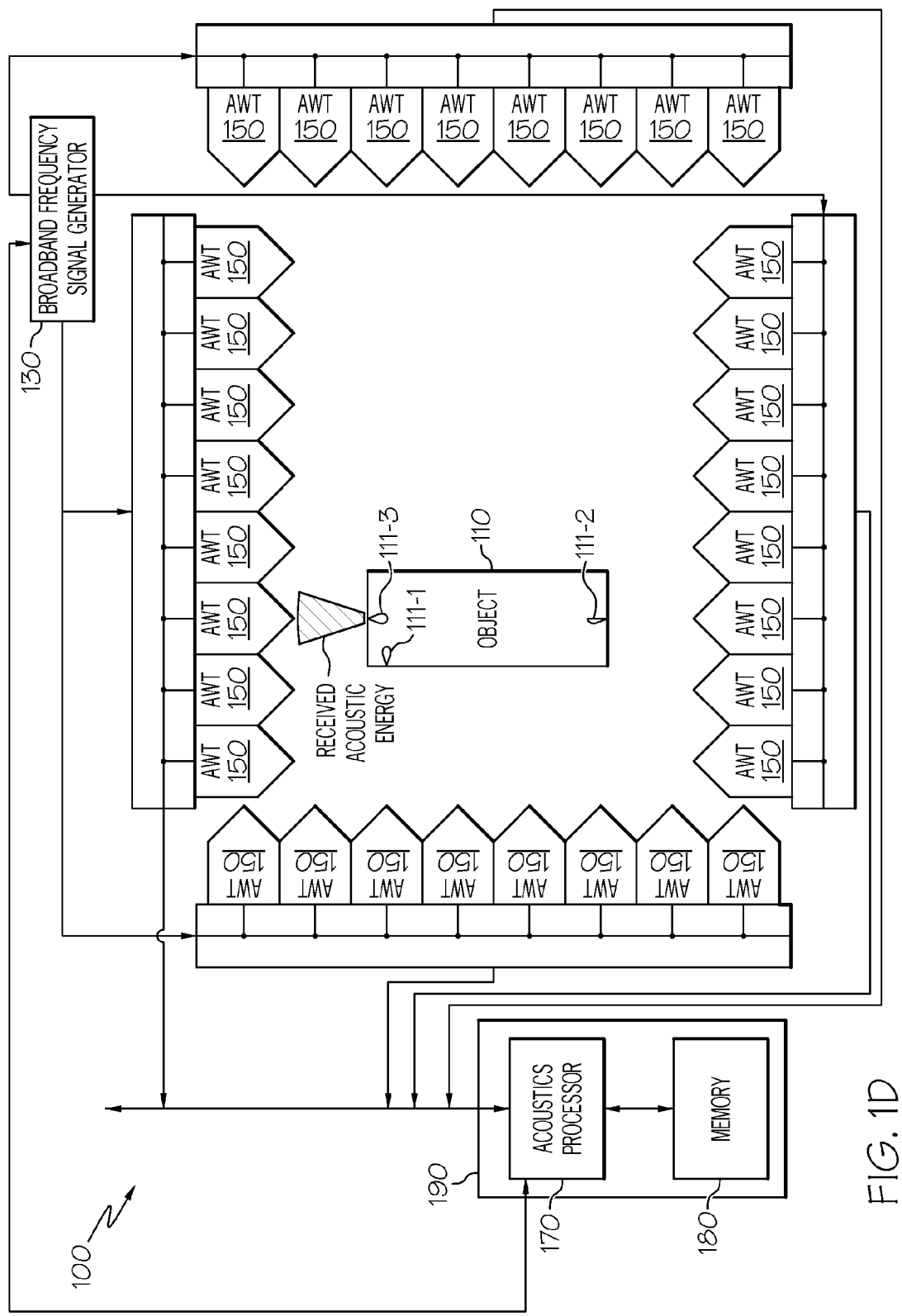
Figure 1E:
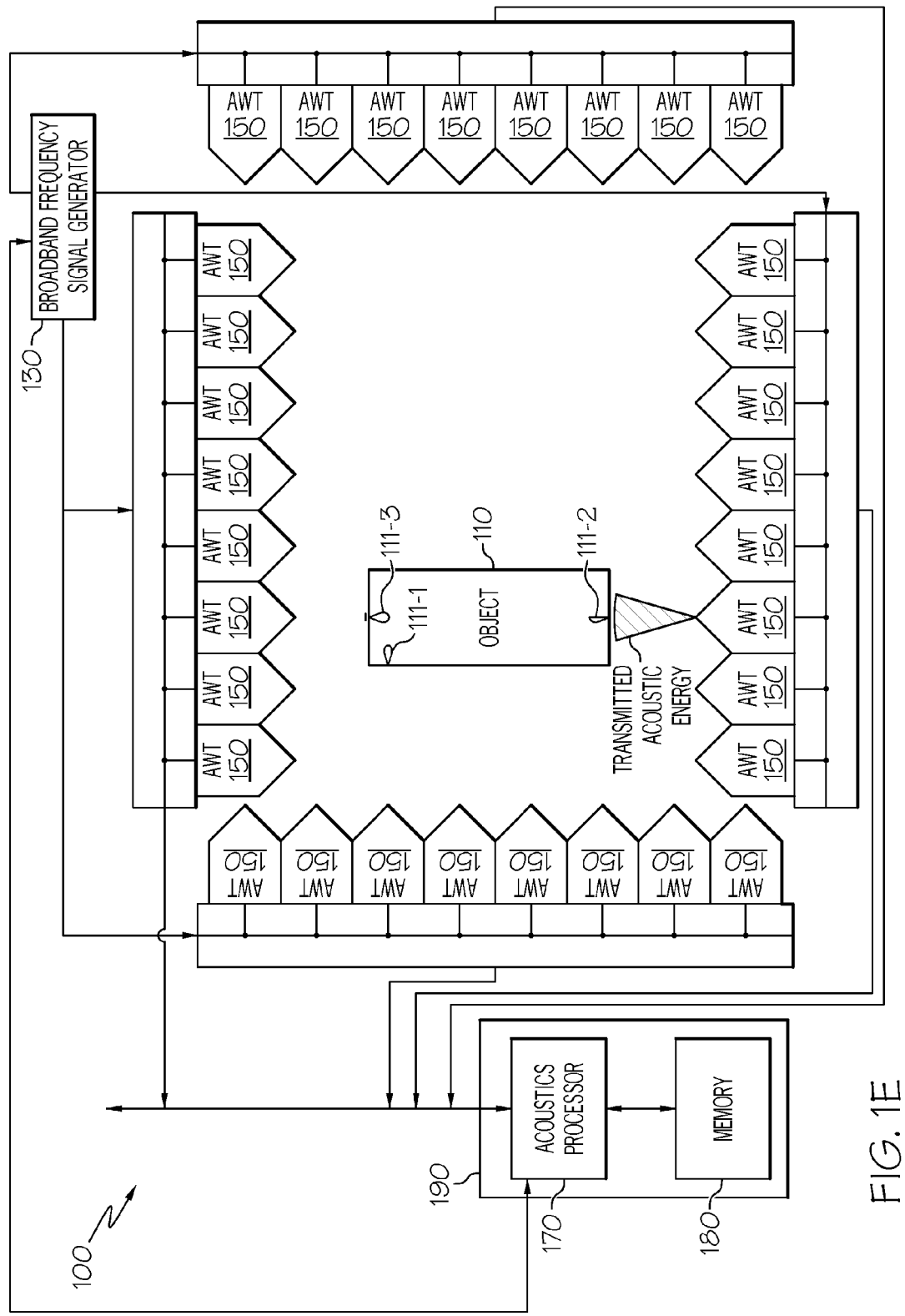
Figure 1F:
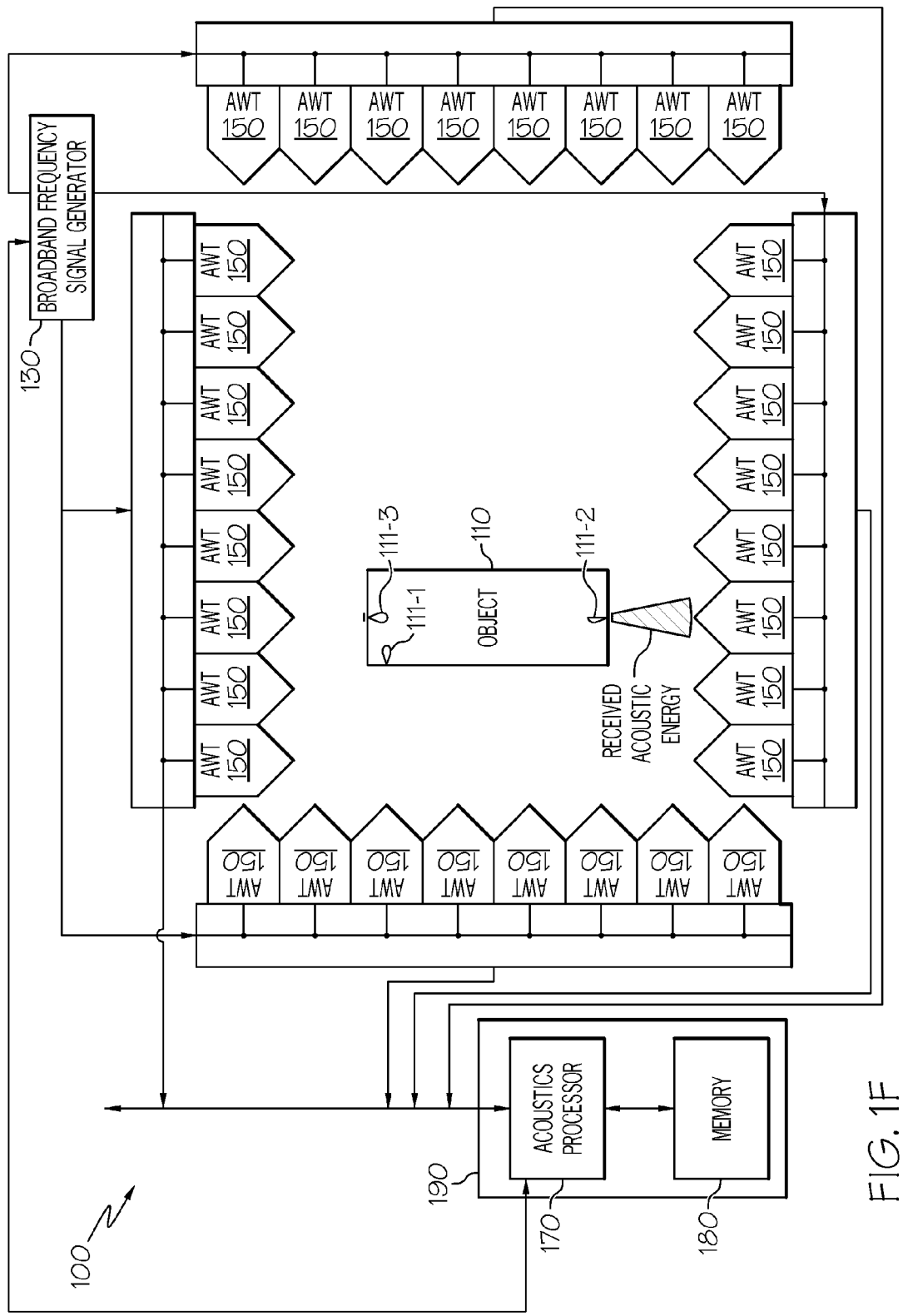

As illustrated in FIGS. 1B, 1D and 1F, each AWT 150 can receive or acquire vibrations induced in the object via acoustic waves. Each of the AWTs 150 can monitor acoustic waves generated by and received from the object 110 in response the transmitted acoustic waves. In other words, in response to the transmitted acoustic waves, each of the AWTs 150 can detect acoustic energy from the object 110. The AWTs 150 are positioned so that the acoustic waves generated by and received from the object 110 can be detected by at least one of the various AWTs 150. By placing AWTs 150 over all regions of interest of the object 110, acoustic energy generated by the object 110 can be detected by the various AWTs 150. A receiver portion of each of the AWTs 150 can include an ultrasonic sound or vibration sensor (e.g., a vibrometer, such as a Doppler laser vibrometer) that is designed to detect acoustic energy that is coupled to them from the object 110 by the received sound waves.

Each AWT 150 can produce a signal that can be processed by the acoustics processor 170 to acquire an acoustic spectral response of the object 110. The acoustics processor 170 is designed to process the received acoustic waves detected by each of the AWTs 170 to generate spectral response data that corresponds to vibration of the object 110 (as detected by each of the AWTs 150). For each particular AWT 150, the acoustics processor 170 can determine, based on the received acoustic waves, a distance between the particular AWT and the object and corresponding resonant frequencies of the object. Acoustic energy in the form of vibrations generated by the object 110 can be received by the AWT 150 as received acoustic waves. The location of a particular AWT 150 with respect to the object 110 determines a relative location of the object 110 with respect to the particular AWT 150, and the frequencies the object 110 vibrates at.

The acoustics processor 170 is also designed to process the spectral response data to determine an optimized setup comprising optimized excitation frequencies and optimized position information. The optimized position information specifies positions of particular AWTs 150 that are associated with regions of interest that correspond to potential locations of defects 111 in the object 110. The acoustics processor 170 can optionally perform additional signal processing on the signals received from the AWTs.

Figure 2A:
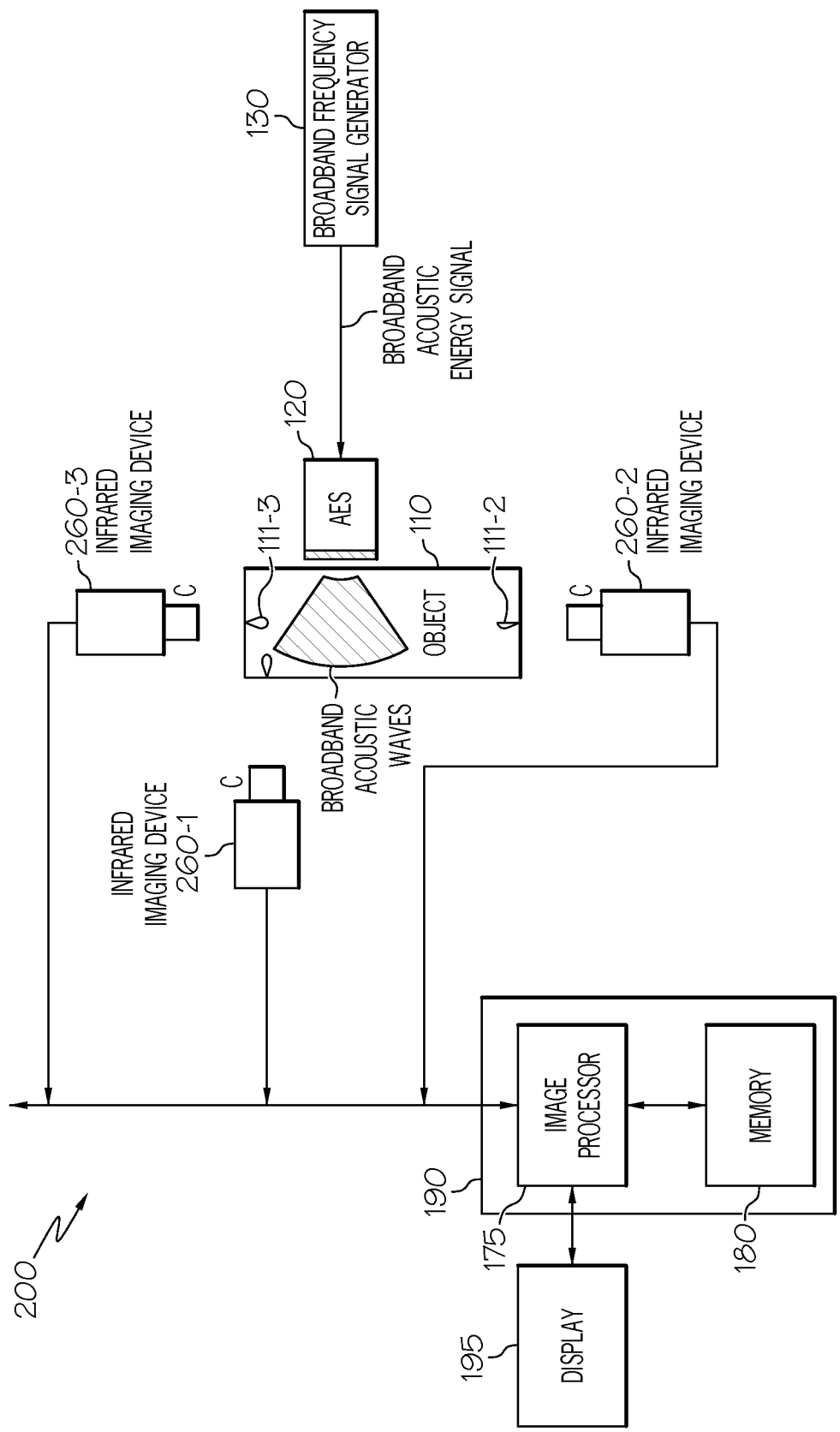
FIGS. 2A and 2B are block diagrams of a system in accordance with an exemplary embodiment after infrared (IR) imaging devices have been selectively positioned at optimized inspection positions.
Figure 2B:
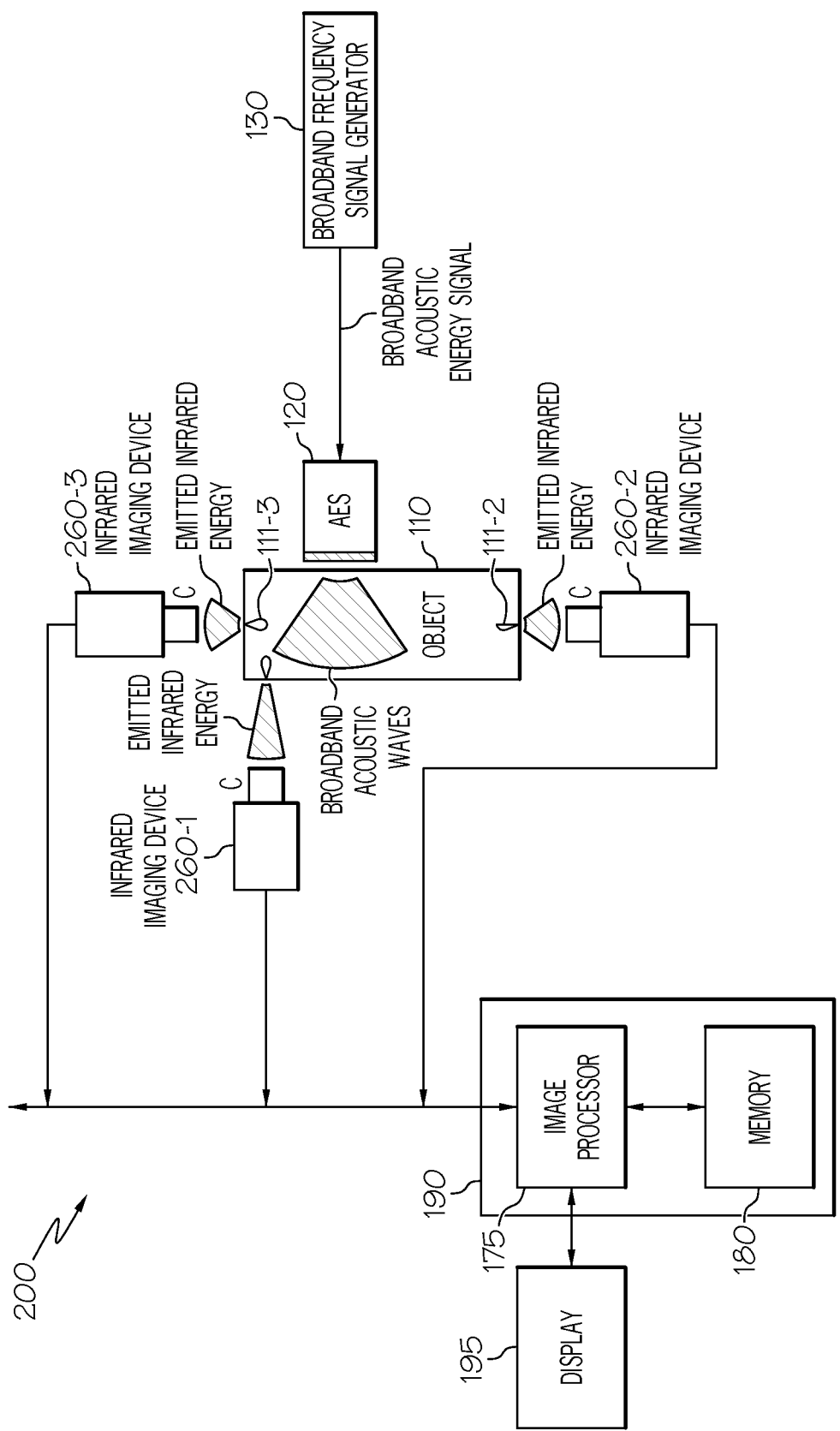

Once the optimized setup information has been determined, it can be used to selectively position a plurality of IR imaging devices 260 with respect to the object 110. FIGS. 2A and 2B are block diagrams of a system 200 that is used in accordance with an exemplary embodiment after the IR imaging devices 260 have been selectively positioned at optimized inspection positions per the optimized setup. The system 200 includes the object 110, an acoustic energy source (AES) 120, the broadband frequency signal generator 130, and IR imaging devices 260.

The acoustic energy source (AES) 120 is acoustically coupled to the object 110. In addition to being acoustically coupled to the object, the AES 120 can be physically/mechanically and/or electrically coupled to the object 110 using any techniques known in the art. The AES 120 can be physically or mechanically coupled to the object 110 at one or more selected locations via physical/mechanical contact. For example, in one embodiment, the ultrasonic energy from the AES 120 can be coupled into the object 110 through a mechanical coupler (not illustrated) that serves as a mechanical contact to the object 110. In other implementations, the AES 120 can be an air-coupled ultrasonic device (e.g., acoustic wave source) that is acoustically coupled to the object 110 over the air. In addition, alternate acoustic generators, such as an inductively coupled device, can be employed as the AES 120 thus obviating the necessity of establishing physical contact between the AES 120 and the object 110. Some non-limiting examples of such coupling techniques are described, for example, in U.S. Pat. No. 7,064,330, entitled "Infrared Defect Detection Via Broad-Band Acoustics," the disclosure of which is incorporated by reference herein in its entirety. In addition, it is noted that in some implementations, multiple AESs 120 can be used that interoperate together to excite the object 110.

The AES 120 can be any ultrasonic transducer capable of generating ultrasonic energy at varying ultrasonic frequencies, power levels and pulse durations. In one implementation, the AES 120 can be implemented using an ultrasonic transducer that generates a sound signal within certain ultrasonic frequency band(s), and couples the sound signal into the object 110. In one embodiment, the AES 120 generates pulses of ultrasonic energy at different excitation frequencies for any applicable period of time at any applicable a power level. However, as will be appreciated by those skilled in the art, other ultrasonic frequencies, power levels and pulse durations can be used within the scope of the present invention. In one specific implementation, such a transducer can include a piezoelectric element that generates ultrasonic energy within a wide frequency band for a length of time.

The AES 120 is designed to transmit acoustic waves to the object 110 that are generated based on another broadband acoustic energy signal from the broadband frequency signal generator 130. The broadband acoustic energy signal from the broadband frequency signal generator 130 comprises the optimized excitation frequencies that will result in optimized interactions (e.g., improved vibration amplitudes) between the object 110 and the acoustic energy source 120 when the acoustic energy source 120 is excited at those optimized excitation frequencies.

The broadband frequency signal generator 130 generates a broadband acoustic energy signal, and the AES 120 transmits it to the AES 120 for a short period of time (e.g., between 0.1 milliseconds and 1 second in one exemplary implementation). The AES 120 couples broadband mechanical energy to the object 110 over a broad spectrum to help ensure a thorough excitation of defects that can potentially resonate at many frequencies. The wide bandwidth of the broadband acoustic energy signal thus provides improved defect detection capability for objects having complex geometrical component structures.

As illustrated in FIG. 2A, acoustic waves from the AES 120 couple acoustic energy to the object 110 to energize defects 111 in the object 110. Defects in the object 110 will heat up and generate heat at levels greater than those that will be generated by non-defective features. The acoustic waves cause each of the defects 111 to vibrate with (or resonate at) greater amplitude than other portions of the object 110 and generate heat as defects 111 heat up in response to the acoustic waves. In FIGS. 2A and 2B, broadband acoustic waves that are coupled to the object 110 by the AES 120 are represented as having a particular profile; however, this is not intended to illustrate an actual representation of the profiles of the broadband acoustic waves. Rather, it is merely intended to represent broadband acoustic waves being transmitted from the AES 120 into and/or towards the object 110. As illustrated in FIG. 2B, the heat generated by the defects results in emission of infrared energy by the object 110 that has a detectable thermal response characterized by a thermal signature that is discernable from other infrared emissions by non-defective portions of the object 110. In FIG. 2B, emitted infrared energy is represented as having a particular profile; however, this is not intended to illustrate an actual representation of the profiles of the emitted infrared energy. Rather, it is merely intended to represent infrared energy being emitted from the object 110 into and/or towards the devices 260. The infrared energy emitted by the object is correlated with the vibrations and heat that are generated by the various defects.

As noted above, in accordance with the disclosed embodiments, the infrared imaging devices 260 can be selectively positioned with respect to the object 110 at optimized inspection positions such that each infrared imaging device 260 is selectively aimed at a particular region of interest of the object 110. The optimized inspection positions can be determined based on the optimized position information for the AWTs 150. Each of the infrared imaging devices 260 is selectively positioned apart from the object 110 so that they are within infrared acquisition range and can detect IR energy emitted by the object 110 so that a thermal image of the object 110 can be generated. In general, the infrared imaging devices 260 can be implemented using any conventional imaging device or system that is capable of detecting/imaging thermal energy. In some implementations, the infrared imaging devices 260 can be implemented using thermal imaging cameras including infrared cameras and/or fiber optic cameras. In one implementation, the infrared imaging devices 260 include one or more capacitive-coupled discharge (CCD) devices that are particularly sensitive to emissions in the infrared range. Any number of IR imaging devices 260 can be used to monitor IR signals generated by defects 111 in the object 110 as the defects 111 vibrate. Although FIGS. 2A-2C each illustrate three different IR imaging devices 260 that are positioned at different optimized inspection positions with respect to the object 110, the number of IR imaging devices 260 and the respective optimized inspection positions are exemplary only and not intended to be limiting. In addition, it is noted that the IR imaging devices 260 are illustrated at different positions in a two-dimensional space due to two-dimensional limitations of the block diagrams; however, those skilled in the art will appreciate that the IR imaging devices 260 can be positioned at any location in a three-dimensional space defined with respect to the object 110.

After excitation, each of the infrared imaging devices 260 can detect the emission of infrared energy by the object 110, and capture infrared images of the portions of the object that they are aimed at. Each of the infrared imaging devices 260 can generate infrared images of a particular region of interest of the object 110 that they are aimed at based on IR signals received from the object as the defects 111 vibrate over a time interval. Each of the plurality of infrared imaging devices 260 can record a time series of such infrared images.

Each of the infrared imaging devices 260 are also designed to capture and record a background image of the object prior to excitation of the object so that the infrared imaging devices 260 have a baseline or reference image of the object 110 prior to excitation. Each of the infrared imaging devices 260 can record images in synchronicity with the AES 120 using a device capable of storing data relating to images that it acquires.

The image processor 175 is coupled to the infrared imaging devices 260. The image processor 175 can process the time series of infrared images in contrast to a background or reference image that was previously recorded (e.g., prior any acoustic induced heating of the defects) to generate a composite infrared image that is indicative of the defects. Using techniques known to those skilled in the art of infrared image processing, the image processor 175 uses the reference image and the time series of infrared images to generate a composite infrared image. The composite infrared image can include portions that represent discernable emissions of an amount of infrared energy by a portion of the object 110 that are indicative of infrared energy emitted by a particular defect in the object 110. These thermal signatures are distinguishable from background infrared energy emitted by the object 110. The composite infrared image information can be captured in memory 180 that can be either located remotely and accessed electronically or located within the infrared imaging devices 260. In addition, the composite infrared image information can be displayed on a display 195.

Figure 3:
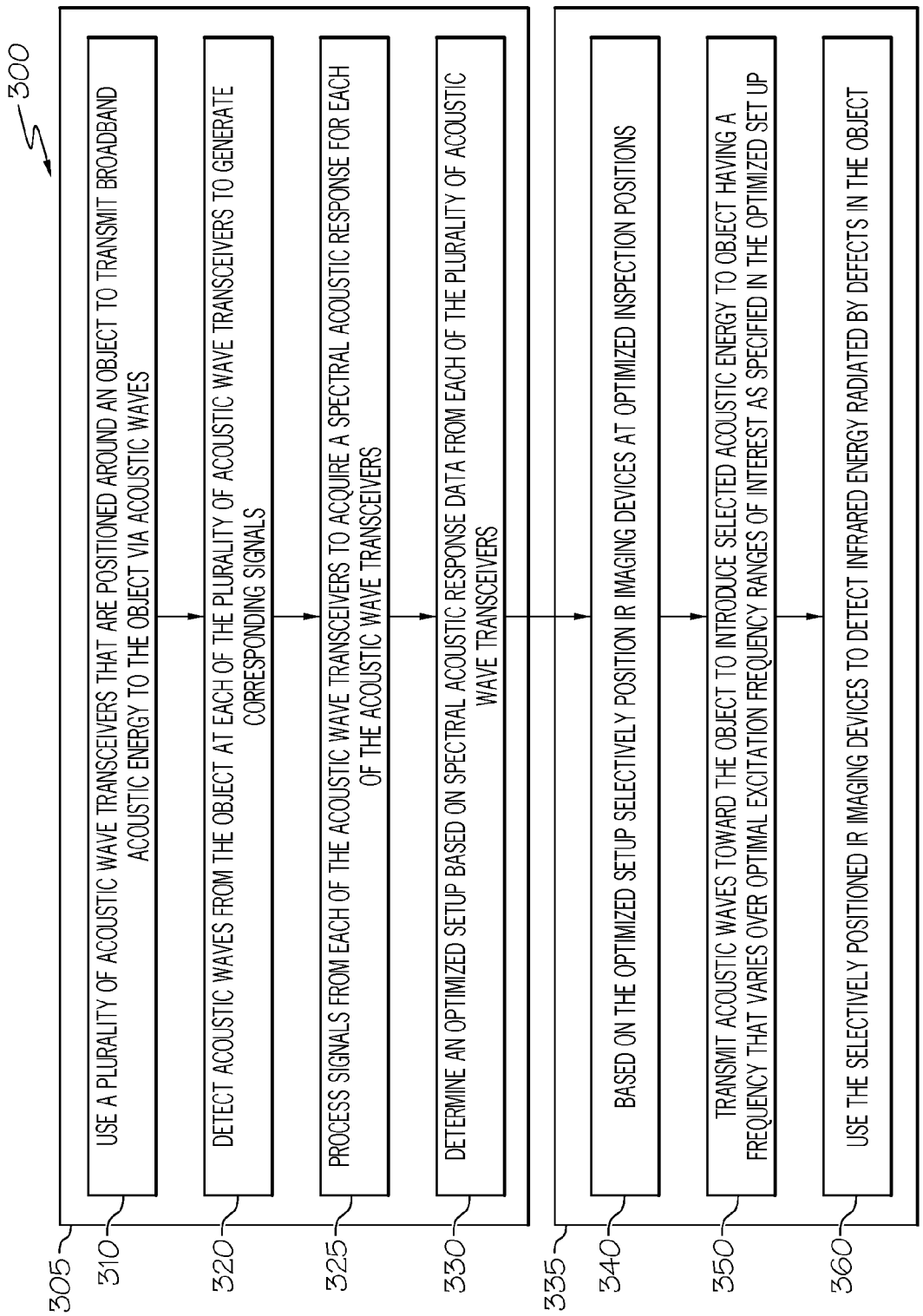
FIGS. 3-6 illustrate a method for detecting defects in an object in accordance with some of the disclosed embodiments.
Figure 5:
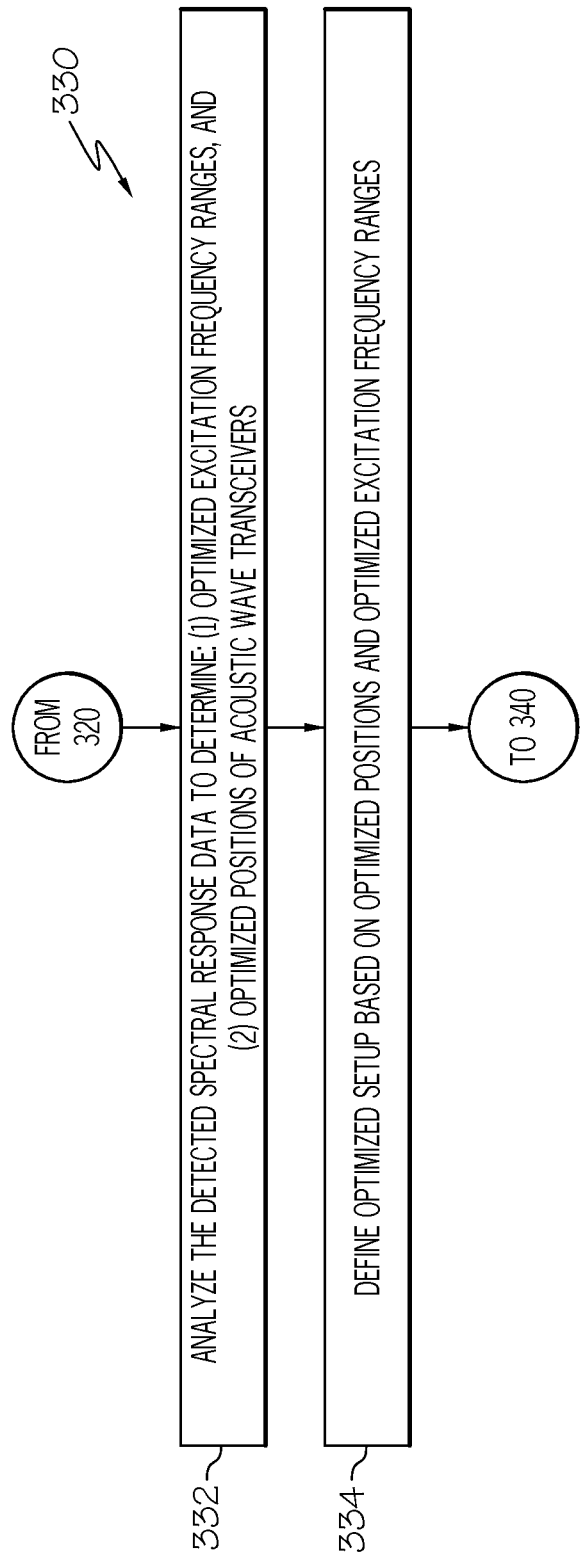
Figure 6:

FIG. 3 illustrates a method 300 for detecting defects 111 in an object 110 in accordance with some of the disclosed embodiments. The method 300 will be described with reference to the systems 100, 200 that are illustrated in FIGS. 1A through 2B. The method 300 includes two phases 305, 335. The first phase 305 includes steps 310, 320, 325, 330, and the second phase 335 includes steps 340, 350, 360. As will be described below, FIG. 4 illustrates one exemplary implementation of step 310 of method 300, FIG. 5 illustrates one exemplary implementation of step 330 of method 300, and FIG. 6 illustrates one exemplary implementation of step 360 of method 300 in accordance with some of the disclosed embodiments.

The first phase 305 begins at step 310, where broadband acoustic energy is sequentially coupled to the object 110 via acoustic waves transmitted by each of the AWTs 150. As described above, this acoustic energy is generated in response to a broadband acoustic energy signal. In accordance with the disclosed embodiments, the excitation frequency of each of the AWTs 150 can be varied over broad bandwidth range of excitation frequencies of potential interest.

Figure 4:
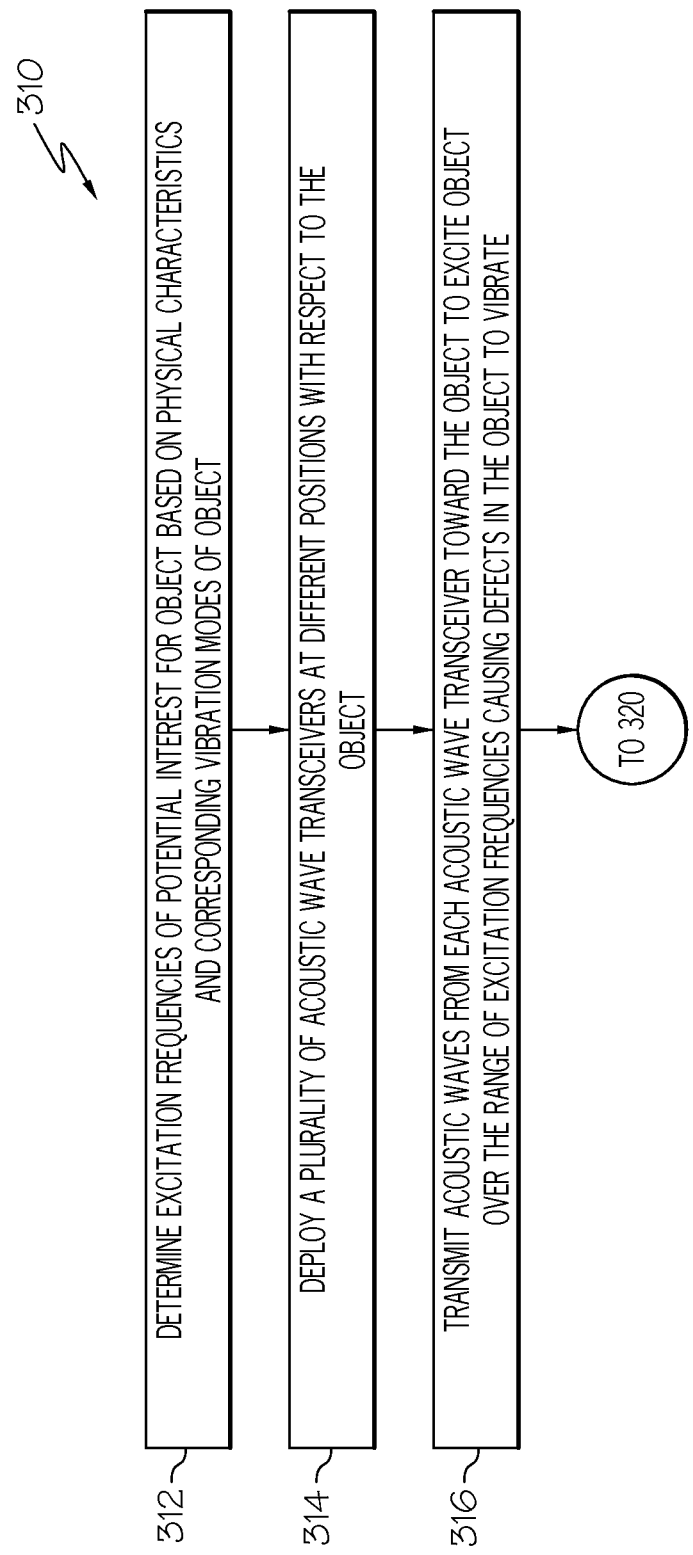

FIG. 4 illustrates one exemplary implementation of step 310 of method 300 in accordance with some of the disclosed embodiments. At step 312, the range of excitation frequencies of potential interest for the object 110 can be determined based on physical characteristics (e.g., shape, weight, dimension, and geometry) of object 110 and corresponding vibration modes of object 110. At step 314, the AWTs 150 can be deployed at different positions with respect to the object 110 that correspond to the regions of interest. By placing AWTs 150 over all regions of interest of the object 110, any emitted acoustic energy generated by the object 110 can be detected. At step 316, acoustic waves are transmitted from a particular AWT 150 toward the object to excite object over the broad bandwidth range of excitation frequencies (as frequency is varied) causing defects 111 in the object 110 to vibrate. The defective features 111 of the object 110 vibrate in response to acoustic waves communicated by each of the AWTs 150. In other words, application of the acoustic energy to the object 110 vibrates defective features in the object 110, which causes defects 111 (e.g., tight cracks) in the object 110 to emit acoustic energy as acoustic waves. Step 316 can be repeated, sequentially, for each of the AWTs 150 in sequence such that each one is excited over the wide bandwidth range of excitation frequencies to cause defective features of the object 110 to vibrate.

At step 320, each of a plurality of AWTs 150 can then detect the acoustic waves received from the object 110 and generate a signal that includes information that can be used to determine an acoustic spectral response of the object. At 325, the acoustics processor 170 can then process signals provided from each of the AWTs 150 to generate a spectral acoustic response for each AWT 150.

Based on spectral acoustic response data, at step 330, an optimized setup can be determined and defined. FIG. 5 illustrates one exemplary implementation of step 330 in accordance with some of the disclosed embodiments. At step 332, the spectral acoustic response data that corresponds to each of the AWTs 150 is analyzed/processed to determine (1) optimized excitation frequency ranges that are to be applied by the acoustic energy source (AES) 120 that will result in optimized interactions (e.g., improved vibration amplitudes) between the AES 120 and object 110, and (2) optimized positions of AWTs 150 that correspond to particular ones of the regions of interest that will result in optimized interactions between the object 110 and particular ones of the AWTs 150. At step 334, the (1) optimized excitation frequency ranges and the (2) optimized positions are used to define the optimized setup. The optimized positions of AWTs 150 and optimized excitation frequency ranges will increase the heat generated by defects 111 in the object 110 due to acousto-thermal effects. Thus, in accordance with embodiments, the potential locations or positions of defects in an object can be determined prior to using the infrared imaging devices 260 to detect the emission of infrared energy that reflects the location of defects 111 in the object 110.

Once the optimized setup is determined, method 300 enters the second phase 335. At step 340, IR imaging devices 260 can be selectively positioned at optimized inspection positions with respect to the object 110. These optimized inspection positions that correspond to and can be determined based on optimized positions of the AWTs 150 that are specified by the optimized setup. These optimized inspection positions correspond to optimized positions of the AWTs 150 such that IR imaging devices 260 are selectively aimed at particular regions of interest of the object 110 where defects 111 have been determined to be most likely. These optimized inspection positions allow the IR imaging devices 260 to focus on regions of interest in the object 110 where defects 111 will most likely exhibit identifiable heat generation due to acousto-thermal effects.

At step 350, broadband acoustic energy is introduced into (e.g., induced in or imparted into) the object 110 via transmission of acoustic waves. As the broadband acoustic energy excites the object 110 to produce mechanical vibrations, defects in the object 110 will vibrate with greater amplitude than other portions of the object 110. Relative motion of the defective features 111 produces heat, which causes an increase in temperature in and around the defects and the emission of infrared energy by the object 110.

At step 360, the selectively positioned IR imaging devices 260, which are aimed at particular regions of interest of the object 110, can then detect infrared energy radiated by defects 111. The intensity of infrared emissions by defects 111 in the object 110 have a detectable thermal response. In other words, infrared emissions by defects 111 can be detected by the IR imaging device as being distinguishable from background infrared energy generated by an object (e.g., have an intensity that is discernable from the intensity of other infrared emissions by non-defective portions of the object 110 in response to the same acoustic energy). Each of the selectively positioned IR imaging devices 260 can capture or acquire a plurality of images of the subsequent infrared emissions from the object 110 over a time interval. Each of the images can include a portion that is indicative of an intensity of infrared energy emitted by one or more defects. Each defect will have a thermal signature that can be read by at least one of the infrared imaging devices 260. The increase in temperature and/or the infrared emissions by defects 111 in the object 110 can be visually detected using infrared imaging equipment, viewed on the display and/or stored. Although not illustrated, the images can be optically recorded, and may also be image processed in real time to display an output image.

FIG. 6 illustrates one exemplary implementation of additional processing that can be performed at and/or after step 360 of method 300 in accordance with some of the disclosed embodiments. At step 362, IR response signals are acquired by each of the IR imaging devices 260 as testing runs over the optimized excitation frequency ranges of interest. Based on IR response signals, at step 364, relationships between positions of the IR imaging devices 260, different excitation frequencies, and resulting thermal responses of the object 110 (e.g., heat generated by the object 110) are determined At step 366, the optimized setup of IR imaging device positions and acoustic energy source (AES) 120 excitation frequency ranges can be determined that provide maximum/optimum acousto-thermal coefficient. This optimized setup can be stored in memory. Based on the thermal responses of the object 110, any defects in the object be determined to be either (1) acceptable, in which case the part is deemed to be accepted, or (2) unacceptable, in which case the part is deemed rejected.

Those of skill would further appreciate that the various illustrative logical blocks, modules, circuits, and algorithm steps described in connection with the embodiments disclosed herein may be implemented as electronic hardware, computer software, or combinations of both. Some of the embodiments and implementations are described above in terms of functional and/or logical block components (or modules) and various processing steps. However, it should be appreciated that such block components (or modules) may be realized by any number of hardware, software, and/or firmware components configured to perform the specified functions. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention. For example, an embodiment of a system or a component may employ various integrated circuit components, e.g., memory elements, digital signal processing elements, logic elements, look-up tables, or the like, which may carry out a variety of functions under the control of one or more microprocessors or other control devices. In addition, those skilled in the art will appreciate that embodiments described herein are merely exemplary implementations.

The various illustrative logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the embodiments disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such the processor can read information from, and write information to, the storage medium. In the alternative, the storage medium may be integral to the processor. The processor and the storage medium may reside in an ASIC. The ASIC may reside in a user terminal In the alternative, the processor and the storage medium may reside as discrete components in a user terminal.

In this document, relational terms such as first and second, and the like may be used solely to distinguish one entity or action from another entity or action without necessarily requiring or implying any actual such relationship or order between such entities or actions. Numerical ordinals such as "first," "second," "third," etc. simply denote different singles of a plurality and do not imply any order or sequence unless specifically defined by the claim language. The sequence of the text in any of the claims does not imply that process steps must be performed in a temporal or logical order according to such sequence unless it is specifically defined by the language of the claim. The process steps may be interchanged in any order without departing from the scope of the invention as long as such an interchange does not contradict the claim language and is not logically nonsensical.

Furthermore, depending on the context, words such as "connect" or "coupled to" used in describing a relationship between different elements do not imply that a direct physical connection must be made between these elements. For example, two elements may be connected to each other physically, electronically, logically, or in any other manner, through one or more additional elements.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A system for detecting defects in an object, the system comprising:
    a phased acoustic array comprising a plurality of acoustic wave transceivers (AWTs) positioned around the object at different positions with respect to the object and with respect to each other;
    a broadband frequency signal generator coupled to each of the AWTs, and being designed to generate a broadband acoustic energy signal;
    an acoustics processor coupled to the plurality of AWTs and to the broadband frequency signal generator, the acoustics processor designed to:
        activate each of the AWTs so that each AWT transmits acoustic waves generated based on the broadband acoustic energy signal toward the object while the plurality of AWTs remain stationary with respect to the object, wherein each of the AWTs detects acoustic waves received from the object that are generated by the object in response to the transmitted acoustic waves as received acoustic waves;
        process the received acoustic waves detected by each of the AWTs to generate spectral response data that corresponds to each of the AWTs; and
        process the spectral response data to determine an optimized setup comprising optimized excitation frequencies and optimized-inspection positions for positioning a plurality of infrared imaging devices at different locations around the object; and
    a plurality of infrared imaging devices configured to be selectively positioned with respect to the object at the optimized inspection positions such that the infrared imaging devices are selectively aimed at one or more particular regions of interest that have been determined to correspond to potential locations of defects in the object.

2. A system according to claim 1, wherein the broadband acoustic energy signal comprises a plurality of excitation frequencies of potential interest that are spread out over a broad bandwidth spectrum that spans frequencies between 1 Hz and 15 MHz, wherein the plurality of excitation frequencies of potential interest are determined based on physical characteristics of object and corresponding vibration modes of object.

3. A system according to claim 1, wherein the transmitted acoustic waves couple broadband acoustic energy to the object generated based on the broadband acoustic energy signal, wherein the broadband acoustic energy causes excitation of the defects such that the defects resonates at different frequencies.

4. A system according to claim 1, wherein the transmitted acoustic waves from a particular AWT excite the object over excitation frequencies of potential interest as frequency is varied to induce motion of the defects and cause the defects to vibrate and generate the received acoustic waves.

5. A system according to claim 1, wherein each of the AWTs detects acoustic energy via the received acoustic waves generated by the object in response to the transmitted acoustic waves to produce a signal that can be processed by the acoustics processor to acquire an acoustic spectral response of the object to the transmitted acoustic waves over the excitation frequencies, wherein the acoustic energy from the object via the received acoustic waves corresponds to vibrations induced in the object.

6. A system according to claim 1, wherein the plurality of AWTs are positioned at different positions around the object so that all regions of interest of the object are within an acoustic field of view of at least one of the AWTs so that acoustic energy emitted by the object via the received acoustic waves can be detected by at least one of the various AWTs.

7. A system according to claim 1, wherein the acoustics processor is designed to determine for each particular AWT, based on the received acoustic waves, a distance between the particular AWT and the object and corresponding resonant frequencies of the object.

8. A system according to claim 1, wherein each of the AWTs comprises an ultrasonic vibration sensor that is designed to detect acoustic energy that is received in the received acoustic waves.

9. A system according to claim 8, wherein each of the AWTs comprises a vibrometer.

10. A system according to claim 1, further comprising:
    an acoustic energy source (AES) that is acoustically coupled to the object and designed to transmit other acoustic waves to the object that are generated based on a second broadband acoustic energy signal to couple acoustic energy to the object, wherein the second broadband acoustic energy signal comprises the optimized excitation frequencies that will result in optimized interactions between and object and the acoustic energy source when the acoustic energy source is excited at the optimized excitation frequencies.

11. A system according to claim 10, wherein the other acoustic waves couple acoustic energy to the object to energize defects in the object and cause each of the defects to vibrate with greater amplitude than other portions of the object and generate heat as defects heat up in response to the other acoustic waves transmitted to the object.

12. A system according to claim 10, wherein the AES is an ultrasonic transducer.

13. A system according to claim 10, wherein heat generated by the defects results in emission of infrared energy by the object that has a detectable thermal response characterized by a thermal signature that is discernable from other infrared emissions by non-defective portions of the object, and wherein each of the plurality of infrared imaging devices are used to record a time series of infrared images of a portion of the object that they are aimed at, and further comprising:
- an image processor coupled to the plurality of infrared imaging devices, wherein the image processor is designed to process the time series of infrared images in contrast to a reference image to generate a composite infrared image that includes the thermal signature that represents a discernable emission of infrared energy by the portion of the object indicative of an amount of infrared energy emitted by a particular defect in the object that is distinguishable from background infrared energy generated by an object.

14. A system according to claim 13, wherein the reference image is recorded prior any acoustic induced heating of the defects.

15. A method for detecting defects in an object, the method comprising:
- providing a plurality of acoustic wave transceivers (AWTs) positioned around the object at different positions with respect to the object and with respect to each other;
- generating a broadband acoustic energy signal comprising a plurality of excitation frequencies of potential interest that are determined based on physical characteristics of object and corresponding vibration modes of object;
- separately and sequentially transmitting acoustic waves from each of the AWTs toward the object that are generated based on the broadband acoustic energy signal, while the plurality of AWTs remain stationary with respect to the object;
- detecting, at each of the AWTs, received acoustic waves generated by the object in response to the transmitted acoustic waves;
- processing the received acoustic waves detected by each of the AWTs to generate spectral response data that corresponds to each of the AWTs;
- processing the spectral response data to determine an optimized setup comprising optimized excitation frequencies and optimized-inspection positions for positioning a plurality of infrared imaging devices at different locations around the object;
- selectively positioning a plurality of infrared imaging devices with respect to the object at the optimized inspection positions such that the infrared imaging devices are selectively aimed at the particular regions of interest of the object that have been determined to correspond to potential locations of defects in the object;
- transmitting other acoustic waves to the object generated based on a second broadband acoustic energy signal that comprises the optimized excitation frequencies that will result in optimized interactions between and object and the acoustic energy source when the acoustic energy source is excited at the optimized excitation frequencies; and
- generating, at each of the infrared imaging devices based on infrared signals received from the object as the defects vibrate over a time interval, a time series of infrared images of the regions of interest.

16. A method according to claim 15, wherein heat generated by the defects results in emission of infrared energy by the object that has a detectable thermal response characterized by a thermal signature that is discernable from other infrared emissions by non-defective portions of the object, the method further comprising:
- recording, at each of the plurality of infrared imaging devices, a time series of infrared images of a portion of the object that they are aimed at; and
- processing the time series of infrared images in contrast to a reference image to generate a composite infrared image that includes the thermal signature that represents a discernable emission of infrared energy by the portion of the object indicative of an amount of infrared energy emitted by a particular defect in the object that is distinguishable from background infrared energy generated by an object.

17. A method according to claim 15, wherein the transmitted acoustic waves couple broadband acoustic energy to the object over excitation frequencies of potential interest, wherein the broadband acoustic energy causes excitation of the defects to induce motion of the defects and cause the defects to vibrate at different frequencies and generate the received acoustic waves, wherein each of the AWTs detects acoustic energy via the received acoustic waves that corresponds to vibrations induced in the object to produce a signal that can be processed to acquire an acoustic spectral response of the object to the transmitted acoustic waves over the excitation frequencies of potential interest.

* * * * *